(12) United States Patent
Scarpellini et al.

(10) Patent No.: US 9,463,213 B2
(45) Date of Patent: Oct. 11, 2016

(54) USE OF DEGARELIX IN THE TREATMENT OF ENDOMETRIOSIS AND RELATED DISEASES

(71) Applicants: Fabio Scarpellini, Roma (IT); Marco Sbracia, Roma (IT)

(72) Inventors: Fabio Scarpellini, Roma (IT); Marco Sbracia, Roma (IT)

( * ) Notice: Subject to any disclaimer, the term of this patent is extended or adjusted under 35 U.S.C. 154(b) by 0 days.

(21) Appl. No.: 14/432,811

(22) PCT Filed: Sep. 25, 2013

(86) PCT No.: PCT/EP2013/002873
§ 371 (c)(1),
(2) Date: Apr. 1, 2015

(87) PCT Pub. No.: WO2014/053223
PCT Pub. Date: Apr. 10, 2014

(65) Prior Publication Data
US 2015/0273012 A1    Oct. 1, 2015

(30) Foreign Application Priority Data

Oct. 2, 2012  (IT) .............................. MI12A001638

(51) Int. Cl.
| A61K 38/00 | (2006.01) |
|---|---|
| A61K 9/00 | (2006.01) |
| A61K 38/09 | (2006.01) |
| A61K 38/08 | (2006.01) |

(52) U.S. Cl.
CPC ............ *A61K 38/09* (2013.01); *A61K 9/0019* (2013.01); *A61K 38/08* (2013.01)

(58) Field of Classification Search
None
See application file for complete search history.

(56) References Cited

U.S. PATENT DOCUMENTS

2005/0282731 A1* 12/2005 Bauer .................. A61K 9/0019
514/10.3

FOREIGN PATENT DOCUMENTS

| WO | 03006049 | 1/2003 |
|---|---|---|
| WO | 2011066386 | 6/2011 |

OTHER PUBLICATIONS

F. Scarpellin, M. Sbracia (Use of depot GnRH antagonist (degarelix) in the treatment of endometriosis recurrence. A controlled trial, ASRM 68TH Annual Meeting vol. 98, No. 3, Sep. 2012, p. 68).*
Nezhat et al. Fertility and Sterility_Vol. 78, No. 4, Oct. 2002, p. 820-824.*
Scarpellin, et al., Use of depot GnRH antagonist (degarelix) in the treatment of endometriosis recurrence. A controlled trial:, ASRM 68th Meeting, vo. 98, No. 3, Sep. 2012 (pp. s68-s68).
Broqua, et al., Pharmacological profile of a new, potent, and long-acting gonadotropin-releaseing hormone antagonist: degarelix:, Journal of Pharmacology and Experimental Therapeutics, vol. 301, No. 1, Apr. 1, 2002, pp. 95-102.
Engel, et al., "Drug Insight: clinical use of agonists and antagonists of luteinizing-hormone-releasing hormone", Nature Clinical Practice Endocrinology & Metabolism, Nature Publishing Group, London, GB, vol. 3, No. 2, Feb. 1, 2007, pp. 157-167.
Mezo, et al., "Luteinizing hormone-releasing hormone antagonists", Expert Opinion of Therapeutic Patents 2009 Informa Healthcare, Gbr, vol. 19, No. 12 Dec. 2009, pp. 1771-1785.
International Search Report of PCT/EP2013/002873 of Jan. 23, 2014.

* cited by examiner

*Primary Examiner* — Jeanette Lieb
(74) *Attorney, Agent, or Firm* — Silvia Salvadori, P.C.; Silvia Salvadori

(57) ABSTRACT

The use of degarelix in the treatment of endometriosis, in particular in the treatment of endometriotic ovarian cysts and recurrent endometriotic lesions following surgery and in the treatment of endometriosis and/or endometriotic ovarian cysts in patients who plan to undergo assisted reproduction, is described, wherein this treatment is performed before the patients are subjected to assisted reproduction; degarelix is administered for this purpose as a single dose of 80-120 mg, preferably 80 mg, subcutaneously.

12 Claims, 3 Drawing Sheets

USE OF DEGARELIX IN THE TREATMENT OF ENDOMETRIOSIS AND RELATED DISEASES

This application is a U.S. national stage of PCT/EP2013/002873 filed on 25 Sep. 2013, which claims priority to and the benefit of Italian Application No. MI2012A001638, filed on 2 Oct. 2012, the contents of which are incorporated herein by reference in their entireties.

FIELD OF APPLICATION

The present invention relates to the use of the active principle degarelix in the treatment of gynaecological diseases, more particularly in the treatment of endometriosis, endometriotic ovarian cysts and recurrent endometriotic lesions following surgery.

PRIOR ART

Degarelix is a depot GnRH antagonist which inhibits secretion of FSH and LH by the hypophysis, binding to the GnRH receptor present on the hypophyseal cells secreting the gonadotropic hormones which control the production of sexual steroid hormones such as estradiol and testosterone produced by the ovaries and testicles.

Degarelix (INN) or degarelix acetate (USAN) (proprietary name Firmagon) is used for the treatment of prostate cancer. The degarelix binds to the gonadotropin release hormone (GnRH) receptors in the hypophysis and blocks their interaction with GnRH. This brings about an immediate and profound reduction in levels of luteinizing hormone (LH) and follicle-stimulating hormone (FSH), with consequent suppression of the production of testosterone, estradiol and other steroid sexual hormones produced by the ovaries and testicles.

In the context of this patent application the term "degarelix" must be understood to include "degarelix acetate".

In 2008 the Food and Drug Administration (FDA) in the United States approved the use of degarelix for the treatment of patients with an advanced form of prostate cancer. Subsequently its use has been approved by the European Commission, on the recommendation of the European Medicines Agency (EMEA), in patients with an advanced state of hormone-dependent prostate cancer.

GnRH antagonists such as degarelix constitute a new type of hormone treatment for prostate cancer. These drugs are synthetic peptides derived from the natural decapeptide GnRH, a hormone produced naturally by the neurons of the hypothalamus. GnRH-antagonists compete with natural GnRH to bind to the specific GnRH receptors in the hypophysis. This reversible binding blocks the production and release of LH and FSH. The reduction in LH and FSH levels brings about a rapid and lasting suppression of the release of testosterone by the testicles and estradiol by the ovaries.

Unlike GnRH agonists, which give rise to initial stimulation of the hypothalamus-hypophysis-gonad axis with an increase in testosterone and estradiol levels due to the massive release of LH and FSH by the hypophysis (so-called flare-up effect), GnRH antagonists do not provoke flare-up and do not induce the release, into the circulation, of FSH and LH by the pituitary gland.

Degarelix is available in a depot or prolonged release formulation, with a long period of bioavailability of the drug in the circulation after administration. From studies performed on healthy women volunteers it was found that the injection of 2.5 mg of degarelix brought about immediate suppression of LH and FSH release and approximately 7 days were required for these hormones to return to base levels (Garcia-Velasco J A et al Reproductive Biomedicine Online 2012, 24, 153-162).

At the present time this drug has not been tested on other hormone-dependent diseases. Among the latter, endometriosis is one of the most widespread.

Endometriosis is a chronic disease of women characterized by the presence outside the uterine cavity of endometrial tissue, i.e. the mucosa which lines the uterine cavity and is developed every month under the control of sexual hormones, predominantly estradiol, and which, if pregnancy does not occur, give rise to menstruation together with a drop in the blood levels of the abovementioned female sexual hormones. Ectopic endometrial tissue may be found in the peritoneal cavity, in the peritoneal organs and viscera, such as the ovaries, the most common site, the bladder, the rectum, the intestines, the serous membrane of the peritoneum, the broad and round ligaments of the uterus, as well as in extraperitoneal organs such as the lungs, the eyes and more rarely the brain. This disease is hormone-sensitive and the ectopic endometrial tissue grows under the stimulus of estradiol, which is cyclically produced by the ovarian follicles. It has been estimated that approximately 10% of the female population of fertile age (that is between first menstruation and the menopause) is affected by endometriosis; it has also been considered that this disease is the main cause of loss of working time due to disease in the United States, because of painful manifestations during the menstrual cycle. This disease takes the form of premenstrual pelvic pains, diffuse and continuing pelvic pain, alterations of the cavity, pain during sexual intercourse, infertility and presence of ovarian masses, endometriotic cysts.

Given its widespread and chronic nature—and very often its incurability—this disease is regarded as a social disease that is life-altering and affects the relationship with society.

The disease may be diagnosed through pelvic echography, magnetic resonance and plasma determination of CA 125, a tumor marker which is also generally higher in women with endometriosis. However certain diagnosis of this disease requires laparoscopic examination with multiple biopsy of the lesions and confirmation by histological examination. The diagnosis of this disease is extremely costly and invasive, requiring many investigations, and requires much time; it should be performed in highly specialized centers so that specific treatment can be associated with the diagnosis. Surgery, preferably laparoscopy, which is the least invasive possible, has always been regarded as the treatment of first intent. Despite this, relapses are very frequent, being around 50% and more 4-5 years after surgery. Also the surgery and the disease itself have an adverse effect on a woman's fertility and her ovarian reserve, that is the number of the ovarian follicles which give rise to ovulation every month and the possibility of becoming pregnant. It has been assessed that endometriosis is the cause of approximately 40% of cases of female infertility.

Another possible treatment for endometriosis is hormone therapy blocking the effect of estradiol or its production. Possible treatments are the contraceptive pill, progestins, or GnRH agonists which block the synthesis of estradiol by the ovaries. All these treatments are however affected by a high percentage of relapses after the various treatments have been suspended.

As mentioned above, endometriotic cysts are one manifestation of endometriosis.

The cysts are hollow formations of various sizes which may contain serous fluid, semi-solid tissue or blood within them. They may appear in different parts of the body. Those in the ovary normally develop during the age of fertility, in pre-puberty or pre-menopause.

Endometriotic cysts account for 20% of ovarian cysts. Generally the endometrial tissues covering the uterine cavity break up during the menstrual cycle; in this case however blood which is not expelled with menstruation accumulates and coagulates, forming cysts, which become increasingly larger after each cycle. Pains may appear before and after the menstrual cycle, together with swelling and tenderness.

The cysts tend to expand within the ovary, pulling and stretching its walls, in some cases often to the point of compromising proper functioning of the organ.

One of the main problems in curing endometriosis lies in the difficult choice which doctors and patients have to make when it is necessary to decide whether to remove an endometriotic ovarian cyst. This operation could compromise the woman's reproductive capacity and as a consequence in some cases it may be decided to postpone surgery, or alternatively, to attempt pharmacological treatment.

Particularly in young women (under 32 years), the removal of small endometriotic cysts may cause very much greater damage (possible risk of infertility) comparison to the removal of larger cysts.

It has been found that the surgical removal of smaller endometriotic cysts gives rise to a greater loss of "follicles" (and therefore oocytes); removing them, therefore, at least partly damages the woman's fertility, while the number of follicles present in larger cysts is smaller, and therefore their removal presents less risk to fertility.

In addition to the risk of compromising or in any event reducing fertility, surgical removal also has a high risk of relapse. Because of this there has recently been a trend towards the pharmacological treatment of endometriotic cysts based on an estroprogestin treatment or a treatment using GnRH-agonists. However both these treatments have the disadvantages mentioned above as regards the treatment of endometriosis in general.

The Applicants disclosed, at the ASRM 68$^{th}$ Annual Meeting, vol. 98, no. 3, Sep. 2012, p. s68, that the monthly administration of 80 mg degarelix for a period of three months resulted in reduction of pain and endometriosis recurrence in patients with severe endometriosis.

Broqua P. et al., "Pharmacological Profile of a New, Potent, and Long-Acting Gonadotropin-Releasing Hormone Antagonist: Degarelix", Journal of Pharmacology and Experimental Therapeutics, vol. 301, no. 1, 1 Apr. 2002, disclose the use of degarelix in sex-dependent steroid pathologies requiring long term inhibition of the gonadotrophic axis such as endometriosis.

WO 2011/066386 described the production method of degarelix and points to its use in the treatment of endometriosis.

Engel J. B. et al., "Drug Insight: clinical use of agonists and antagonists of luteinizing-hormone-releasing hormone"; Nature Clinical Practice Endocrinology 86 Metabolism, Nature Publishing Group, Vol. 3, no. 2, Jan. 2, 2007, disclose the use of degarelix in the treatment of endometriosis.

The problem underlying the present invention is that of providing a new, improved, treatment for endometriosis and in particular endometriotic ovarian cysts which overcomes the disadvantages associated with the previously known surgical or pharmacological treatments and as a result of which a woman's ovarian reserve may be best preserved.

SUMMARY OF THE INVENTION

The abovementioned problem has been resolved by providing the GnRH-antagonist degarelix for use in the treatment of endometriosis, wherein degarelix is administered as a single dose of 80-120 mg, preferably as a single dose of 80 mg, every fourth month.

In another aspect the present invention provides the GnRH-antagonist degarelix for use in the treatment of endometriotic ovarian cysts, wherein degarelix is administered as a single dose of 80-120 mg, preferably as a single dose of 80 mg, every fourth month.

In a further aspect the present invention provides the GnRH-antagonist degarelix for use in the treatment of recurrent endometriotic lesions following surgery, wherein degarelix is administered as a single dose of 80-120 mg, preferably as a single dose of 80 mg, every fourth month.

In another aspect the present invention provides the GnRH-antagonist degarelix for use in the treatment of endometriosis and/or endometriotic ovarian cysts in patients who plan to undergo assisted reproduction, in which this treatment is performed prior to subjecting the patients to assisted reproduction and wherein degarelix is administered as a single dose of 80-120 mg, preferably as a single dose of 80 mg, every fourth month.

In order to perform the above treatments, the degarelix is preferably administered subcutaneously.

Preferably the degarelix is administered in the form of an aqueous solution containing 20 mg of degarelix/ml (in the form of acetate) and possible excipients, particularly mannitol, for adjustment of the isotonicity.

The administration of degarelix, under the regimen specified above, to patients with endometriosis has been particularly advantageous in comparison with other previously known forms of treatment.

It has in fact been found that hypophyseal suppression is rapidly brought about, with a quick fall in the levels of FSH and LH and consequent immediate reduction of the circulating estradiol; in addition it has been found that the flare-up effect which was observed with GnRH-agonists and which gives rise to a temporary increase in FSH, LH and estradiol, which could assist development of the disease in addition to reducing the efficacy of treatment, was not present.

Contrary to what has been observed in the treatment with GnRH agonists, a marked lowering of the LH blood levels has been noted, this giving rise to a significant lowering of the blood levels of circulating androgens, which are likely to be converted peripherally into estrogens either by adipose tissue or by the endometriotic lesions themselves; as a consequence more marked hypoestrogenism has been noted, which in the treatment with GnRH-agonists can only be achieved with the addition of other drugs such as aromatase inhibitors (e.g. letrozole or anastrozole).

A considerable advantage of the use of degarelix in comparison with treatments of the known art lies in the fact that just one administration of the drug in a typical dosage of 80-120 mg is sufficient to have an effect which lasts for at least three months, with marked hypoestrogenism and hypoandrogenism in women, and a corresponding reduction in the costs of treatment.

Efficacy of the treatment proposed in the present application has also been found in patients with recurrence of the disease following surgery or previous treatment with GnRH-agonists or estro-progestins (contraceptive pill).

Finally, the treatment proposed in the present invention has also proved effective in the treatment of patients with ovarian endometriosis who wish to receive in vitro fertilization treatment before undergoing surgery or who do not wish to undergo surgery, because the rapid and marked hypoestrogenism, lasting at least three months, achieved with this treatment often brings about a control of the symptoms of the disease.

DETAILED DESCRIPTION

Further characteristic features and advantages of the present invention will become apparent from the examples provided below by way of illustration and without limitation.

EXAMPLE 1

In this experiment the use of degarelix was studied, administered in a dose of 80 mg in a single infusion, with an effect which lasted for at least 4 months (period of amenorrhea and hypoestrogenism), comparing this with the effect of treatment with leuprolide acetate GnRH-agonist administered in a dose of 3.75 mg per month for at least 6 months in women with recurrent endometriosis after surgery and post-surgery treatment with estro-progestins.

30 women divided into two groups of 15 patients each, with recurrent endometriosis after previous surgery for endometriotic cysts, in whom new ovarian cysts, pelvic pain and a rise in plasma CA125 values occurred, were included in the study. One group of patients was treated with 80 mg degarelix acetate in a single subcutaneous injection (Firmagon 80 mg, company Ferring) on the first day of the menstrual cycle, while the other group was treated with leuprolide acetate (Enantone 3.75, Takeda) in a dose of 3.75 mg subcutaneously every month for four months. Both the groups were monitored for FSH, LH, estradiol, androstenedione, dehydroandrostenedione (DEA) and CA125, with plasma doses every fifteen days starting from the day following administration of the drug. Pelvic pain levels experienced by the patients during treatment and during the six months following suspension of the treatment were also evaluated using a "Visual Analogue Scale" (VAS) in which the patient expressed the level of pain experienced on a 10 cm scale.

Figure 1:
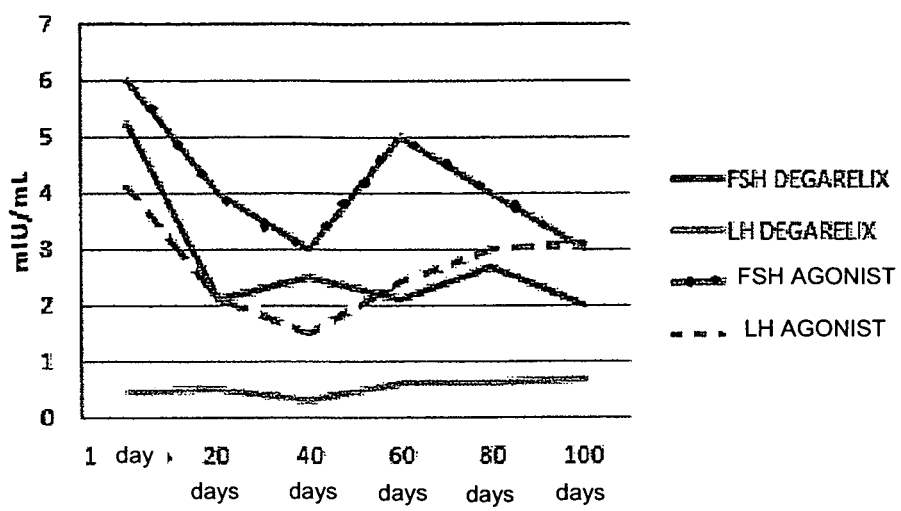
FIG. 1 is a diagrammatic illustration of results of the experiments according to Example 1 described below.
Figure 2:
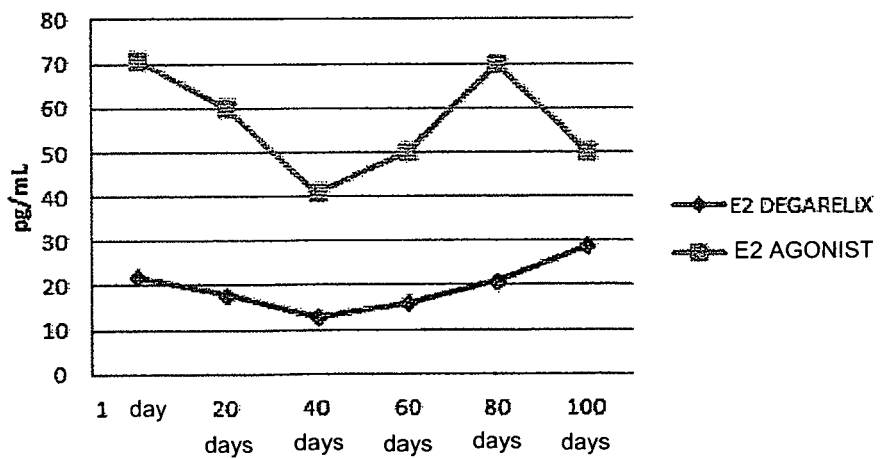
FIG. 2 is a diagrammatic illustration of further results of the experiments according to Example 1 described below.
Figure 3:
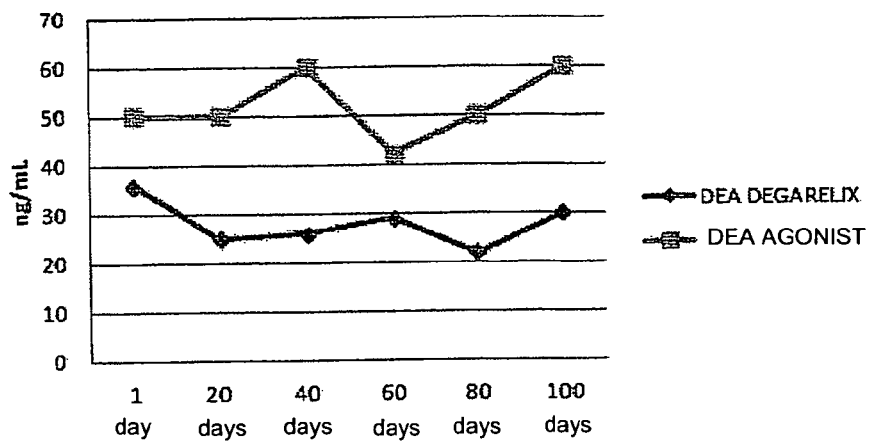
FIG. 3 is a diagrammatic illustration of further results of the experiments according to Example 1 described below.
Figure 4:
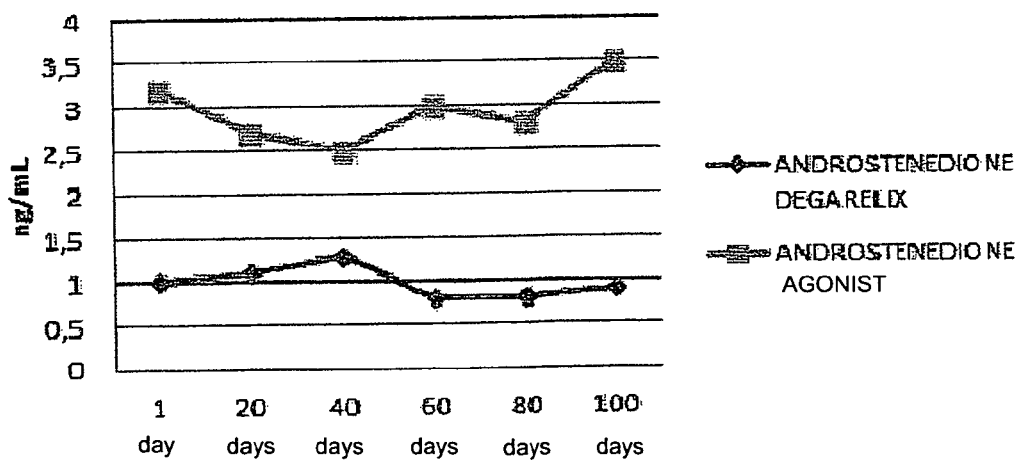
FIG. 4 is a diagrammatic illustration of further results of the experiments according to Example 1 described below.

The results showed that a single administration of 80 mg degarelix acetate made it possible to achieve stable suppression of FSH, LH, estradiol and androgen levels for 4 months, while in the group treated with GnRH-agonist the effect was achieved with 6 administrations. More rapid and stable suppression of LH and FSH (FIG. 1) and lower levels of estradiol (FIG. 2) and androgens (FIGS. 3 and 4) were found in the patients treated with 80 mg degarelix acetate than in those treated with the agonist (P<0.01).

Figure 5:
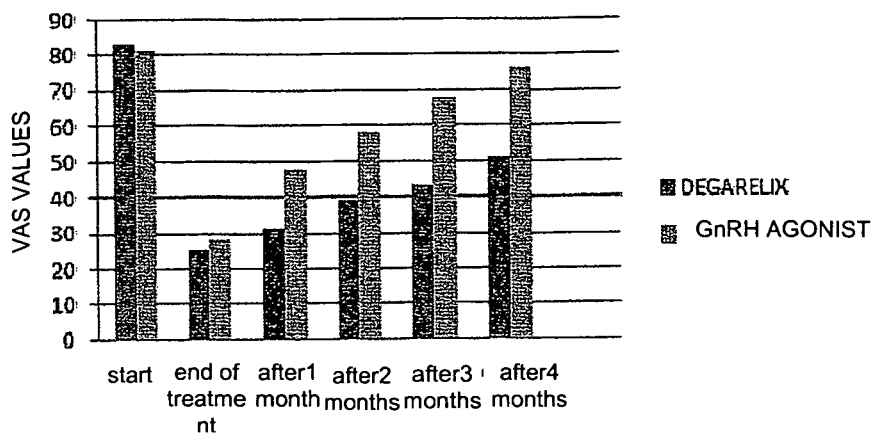
FIG. 5 is a diagrammatic illustration of further results of the experiments according to Example 1 described below.

Table 1 below shows the clinical results of the study, which show how better results in the treatment of patients with recurrent endometriosis were obtained with degarelix than by treatment with GnRH agonist. Furthermore, study of pain in these patients confirmed that degarelix brought about better control of painful symptoms (FIG. 5).

TABLE 1

|  | Degarelix acetate | Leuprolide acetate | P |
|---|---|---|---|
| Disappearance of pain | 1.4 ± 0.3 | 3.8 ± 0.8 | 0.01 |
| CA-125 at the end of treatment | 12.6 ± 10.1 | 34.0 ± 12.7 | 0.01 |
| CA-125 after 2 months | 32.4 ± 21.4 | 52.6 ± 31.5 | 0.01 |
| Disappearance of symptoms at the end of treatment | 93.3% | 60.0% | 0.01 |
| Recurrence six months after the end of treatment | 6.6% | 33.3% | 0.01 |

EXAMPLE 2

In this experiment, 12 patients suffering from endometriosis with the presence of bilateral ovarian cysts who wished to receive a cycle of assisted reproduction underwent, prior to undergoing controlled ovarian hyperstimulation, treatment with 80 mg degarelix acetate in a single administration 4 months before the assisted reproduction cycle, in order to evaluate the efficacy of this treatment on the reduction and/or disappearance of the ovarian cysts without performing surgery.

12 patients with bilateral endometriotic cysts (cysts larger than 3 cm) and high plasma CA125 (over 60 IU/ml) were selected. 80 mg degarelix acetate (Firmagon 80 mg) was injected into the patients on the first day of the cycle and the patients were then monitored for FSH, LH and estradiol values every 20 days, with an echography check to evaluate the dimensions of the cysts.

Figure 6:
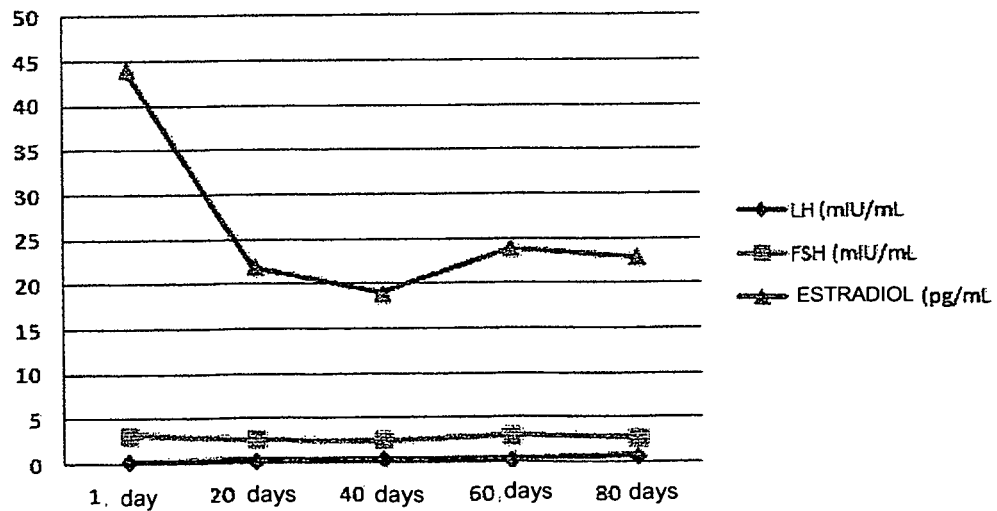
FIG. 6 is a diagrammatic illustration of results of the experiments according to Example 2 described below.

As shown in FIG. 6, low levels of FSH, LH and estradiol were still present 3 months after treatment, while the volume of the endometriotic cysts had decreased significantly, disappearing completely in at least 4 patients. On reappearance of the menstrual cycle the patients began treatment with gonadotropin (Gonal F, Merck-Serono) to induce multiple follicular growth for a cycle of assisted reproduction.

All the patients completed ovarian stimulation with oocyte sampling without showing any recurrence of endometriotic cysts.

Pregnancy was achieved in 5 cases.

The results obtained show that with the degarelix treatment as outlined above it is possible to achieve the rapid regression of ovarian cysts, sufficient to allow an attempt at assisted reproduction without subjecting the patient to surgery and thus safeguarding the ovarian reserve.

Other experiments carried out on patients with recurrent endometriosis as in Example 1 and on patients suffering from endometriosis with the presence of bilateral ovarian cysts as in Example 2, involving the subcutaneous administration of degarelix at a single dose of 100 mg and 120 mg respectively, provided similar results to those reported for Examples 1 and 2.

The invention claimed is:

1. A method of treating endometriosis in patients in need thereof, said method comprising: administering a single dose of 80-120 mg of degarelix every fourth month to said patients; and treating said endometriosis in said patients.

2. The method according to claim 1, wherein degarelix is administered as a single dose of 80 mg every fourth month.

3. A method of treating endometriotic ovarian cysts in patients in need thereof, said method comprising: administering a single dose of 80-120 mg of degarelix every fourth month to said patients; and treating said endometriotic ovarian cysts in said patients.

4. The method according to claim 3, wherein degarelix is administered as a single dose of 80 mg every fourth month.

5. A method of treating recurrent endometriotic lesions following surgery in patients in need thereof, said method comprising: administering a single dose of 80-120 mg of degarelix every fourth month to said patients; and treating said endometriotic lesions following surgery in said patients.

6. The method according to claim 5, wherein degarelix is administered as a single dose of 80 mg every fourth month.

7. A method of treating endometriosis and/or endometriotic ovarian cysts in patients who plan to undergo assisted reproduction, wherein said method is carried out prior to subjecting said patients to said assisted reproduction, said method comprising: administering a single dose of 80-120 mg of degarelix every fourth month to said patients; and treating said endometriosis in said patients.

8. The method according to claim 7, wherein degarelix is administered as a single dose of 80 mg every fourth month.

9. The method according to claim 1, wherein degarelix is administered subcutaneously.

10. The method Degarelix according to claim 9, wherein degarelix is administered in the form of an aqueous solution containing 20 mg degarelix/ml.

11. The method according to claim 10, wherein said aqueous solution contains at least one excipient for the adjustment of isotonicity.

12. The method according to claim 11, wherein said at least one excipient for the adjustment of isotonicity consists of mannitol.

* * * * *